US00PP08144P

United States Patent [19]

Holtkamp, Sr.

[11] Patent Number: Plant 8,144

[45] Date of Patent: Feb. 16, 1993

[54] AFRICAN VIOLET PLANT NAMED TOKYO

[76] Inventor: Reinhold Holtkamp, Sr., Blumenstrasse 28, D 4242 Rees-Haffen, Fed. Rep. of Germany

[21] Appl. No.: 736,220

[22] Filed: Jul. 26, 1991

[51] Int. Cl.[5] ..... A01H 5/00

[52] U.S. Cl. ..... Plt./69.1

[58] Field of Search ..... Plt./69.1, 69.2

*Primary Examiner*—James R. Feyrer

*Attorney, Agent, or Firm*—Foley & Lardner

[57] ABSTRACT

A new and distinct cultivar of African violet named Tokyo characterized by its extra large growth habit (35–40 cm in diameter); single violet-shaped, apple blossom pink flowers with darker center; elongated petals; strong stems which curve toward the center to form a bouquet above the leaves; profuse flowering; large, bright green, oval to spear-shaped leaves; flowering 12–13 weeks after planting of unrooted shoot, and by its long lasting and non-dropping flowers.

1 Drawing Sheet

The present invention comprises a new and distinct cultivar of African violet plant, botanically known as *Saintpaulia ionantha*, and hereinafter referred to by the cultivar name Tokyo.

The new cultivar was referred to during the breeding and selection process by the designation 906 L.M. apf. bl. and is a product of a planned breeding program. The cultivar was originated from a cross made by me in the controlled breeding program in Haffen, Federal Republic of Germany. The female, or seed parent, was a cultivar designated Arizona/6/III. The male, or pollen parent, was a cultivar designated 287 rot rosa w.

Tokyo was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Tokyo has not been observed under all possible environmental conditions. The phenotype may vary significantly with variations in environment such as temperature, light intensity and day length. The following observations, measurements and values describe the new cultivar as grown in a 15 cm pot in Haffen, West Germany and Nashville, Tenn. under greenhouse conditions which closely approximate those generally used in commercial practice.

The following traits have been repeatedly observed and are determined to be basic characteristics of Tokyo, which in combination distinguish this African violet as a new and distinct cultivar:

1) Tokyo will grow as large as 30–40 cm in diameter.
2) Single violet-shaped, apple blossom pink flowers.
3) Strong, wirelike and upright flower stems curving toward the center.
4) First flash of flowers forms a bouquet above the leaves.
5) Profuse flowering.
6) Each plant carries 12–14 and more upright flower stems each of which carries 13–16 and more flowers.
7) Long lasting, non-dropping flowers.
8) Plant saleable 12 to 13 weeks after planting of unrooted shoot.

9) Seed capsules push slightly through.
10) Large, bright green, oval to spear-shaped leaves.
11) After maturity the flowers dry off, and remain on the peduncle without becoming infected by botrytis.

The accompanying color photographic drawing shows a typical specimen plant of the new cultivar grown in a 15 cm pot. The colors appearing in the photograph are as true as possible with color illustrations of this type.

In the following description, color references are made to The Royal Horticultural Society Colour Chart (R.H.S.), except where general colors of ordinary significance are referred to. Color values are taken under natural sunlight conditions at approximately 12 p.m. in Nashville, Tenn.

Botanical classification: *Saintpaulia ionantha*, Ramat., c.v. Tokyo.

Parentage:

*Male parent.*—287 rot rosa w.

*Female parent.*—Arizona/6/III.

Propagation: The new cultivar holds its distinguishing characteristics through successive propagations by leaf cuttings.

Plant: From 10 cm to 13 cm tall when grown in pots, and 30–40 cm in diameter when fully grown.

Leaves:

*General form.*—Oval to spear-shaped.

*Diameter.*—75–85 mm wide and 85–95 mm long.

*Texture.*—Leatherlike.

*Aspect.*—Hairy, shiny.

*Veins.*—Upperside: visible; underside: well pronounced, light green (on young leaves purplish green), shiny.

*Color (upperside).*—Yellow-green group 147 A to B.

*Color (underside).*—Yellow-green group 148 D with touches of greyed-purple group 186 C to D. Young leaves are greyed-purple group 186 A.

*Petiole.*—Strong, brownish green, hairy.

Flowers:

*Buds.*—Size: 8–10 mm just before opening. Shape: Bell-shaped. Color: Pinkish green.

*Sepals.*—Five (5). Color: Brownish green.

*Calyx.*—Shape: Funnel-shaped. Aspect: Spear-shaped, hairy.

*Peduncle.*—Character: Strong upright, hairy. Color: Brownish green.

Individual flowers:

*Size.*—38–42 mm.

*Shape.*—Single violet-shaped (having 3 large and 2 very small petals). The petals are elongated.

*Color (upperside).*—Red-purple group 65 C to D with center being touch of red-purple group 73 A. Under cooler temperatures and more intensive lighting, the apple blossom pink tends to intensify.

*Color (underside).*—Red-purple group 65 C to D.

*Borne.*—Each flower stem carries 13–16 and more flowers on strong, upright peduncles that are free standing above the leaves, thereby forming a bouquet.

*Flowering habit.*—Flowers 12–13 weeks after planting an unrooted plantlet.

Reproductive organs:

*Stamens.*—Two (2). Anthers: 2 composed of 4 anther cells, seed capsule pushes slightly through.

*Filaments.*—Yellowish green, 3–4 mm long.

*Styles.*—5–6 mm long, light pink, base of ovary light green and hairy.

Roots: Normally developed, white when young, turning slightly brownish when older.

Disease resistance: Up to date, Tokyo has shown very good resistance to all major violet diseases.

GENERAL OBSERVATIONS

Tokyo is a very attractive cultivar due to its extra large growth habit. It is designed to be grown in a 15 cm pot (instead of the regular 10 cm pot) and will grow as large as 35–40 cm in diameter. (The diameter can vary depending on how firmly the potting medium is compressed). A nice bouquet of flowers free standing above the leaves develops 12–13 weeks after planting an unrooted plantlet. Each of the 12–14 and more strong flower stems carries 13–16 and more single violet-shaped, apple blossom pink flowers with darker pink center radiating into the two smaller petals. The size difference between the large and small petals is quite noticeable and the petals are elongated. The flowers are long-lasting and non-dropping. The bouquet is surrounded by large, bright green, oval to spear-shaped leaves.

I claim:

1. A new and distinct cultivar of African violet named Tokyo, as described and illustrated, and particularly characterized by its extra large growth habit (35–40 cm in diameter); single violet-shaped, apple blossom pink flowers with darker center; elongated petals; strong stems which curve toward the center to form a bouquet above the leaves; profuse flowering; large, bright green, oval to spear-shaped leaves; flowering 12–13 weeks after planting of unrooted shoot, and by its long lasting and non-dropping flowers.

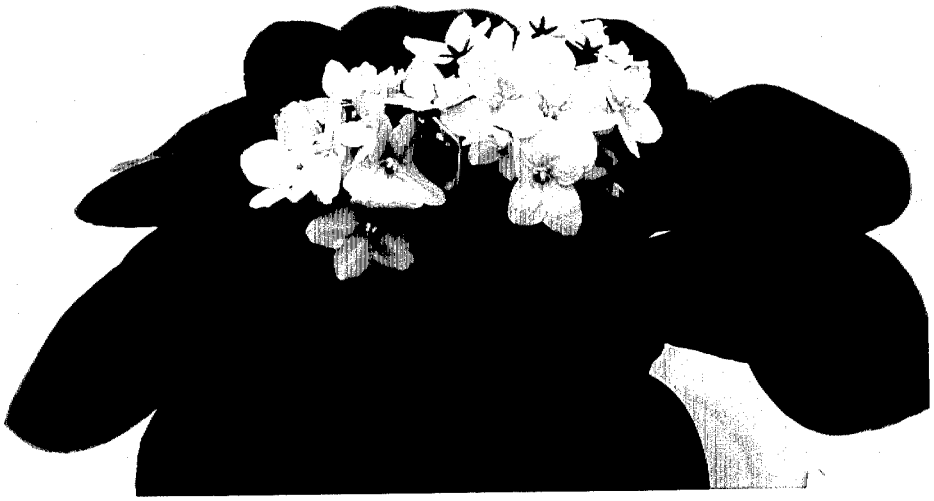

* * * * *